United States Patent [19]

Calkin

[11] Patent Number: 4,665,908
[45] Date of Patent: May 19, 1987

[54] EXTRICATION AND SPINAL RESTRAINT DEVICE

[76] Inventor: Carston R. Calkin, 14880 SW. 83rd Ave., Tigard, Oreg. 97224

[21] Appl. No.: 743,431

[22] Filed: Jun. 11, 1985

[51] Int. Cl.$^4$ .............................................. A61F 13/00
[52] U.S. Cl. .................................... 128/134; 5/82 R; 128/88; 128/89 A
[58] Field of Search .................... 128/78, 87, 75, 87 B, 128/82 R, 88, 82 B, 89 R, 89 A, 134, DIG. 6, DIG. 23; 5/82 R; 2/44

[56] References Cited

U.S. PATENT DOCUMENTS

| | | | |
|---|---|---|---|
| 3,737,923 | 6/1973 | Prolo | 128/78 X |
| 3,889,668 | 6/1975 | Ochs et al. | 2/44 X |
| 4,099,524 | 7/1978 | Cueman et al. | 128/78 |
| 4,211,218 | 7/1980 | Kendrick | 5/82 R X |
| 4,259,950 | 4/1981 | Klippel | 128/134 X |
| 4,299,211 | 11/1981 | Doynow | 128/89 R |
| 4,506,664 | 3/1985 | Brault | 128/134 |
| 4,580,555 | 4/1986 | Coppess | 128/89 R |
| 4,601,075 | 7/1986 | Smith | 5/82 R |

Primary Examiner—Edgar S. Burr
Assistant Examiner—Moshe I. Cohen
Attorney, Agent, or Firm—Olson and Olson

[57] ABSTRACT

An extrication and spinal restraint device for use in emergency rescues and onsight medical aid where potential back, neck and shoulder injuries may exist comprises a jacket of flexible material which is arranged to extend the entire length of a victim's spine, neck and head and be secured thereto by head, torso and leg straps. The flexible jacket mounts a pair of rigid back brace boards arranged to be disposed behind a victim's back, neck and head and configured to extend along the victim's spine to provide rigid support only inwardly of the sides of the victim's body and head. A removable shoulder board may be attached to the spinal restraint device to support and restrain the victim's shoulders immovably in a flat, outstretched condition.

9 Claims, 8 Drawing Figures

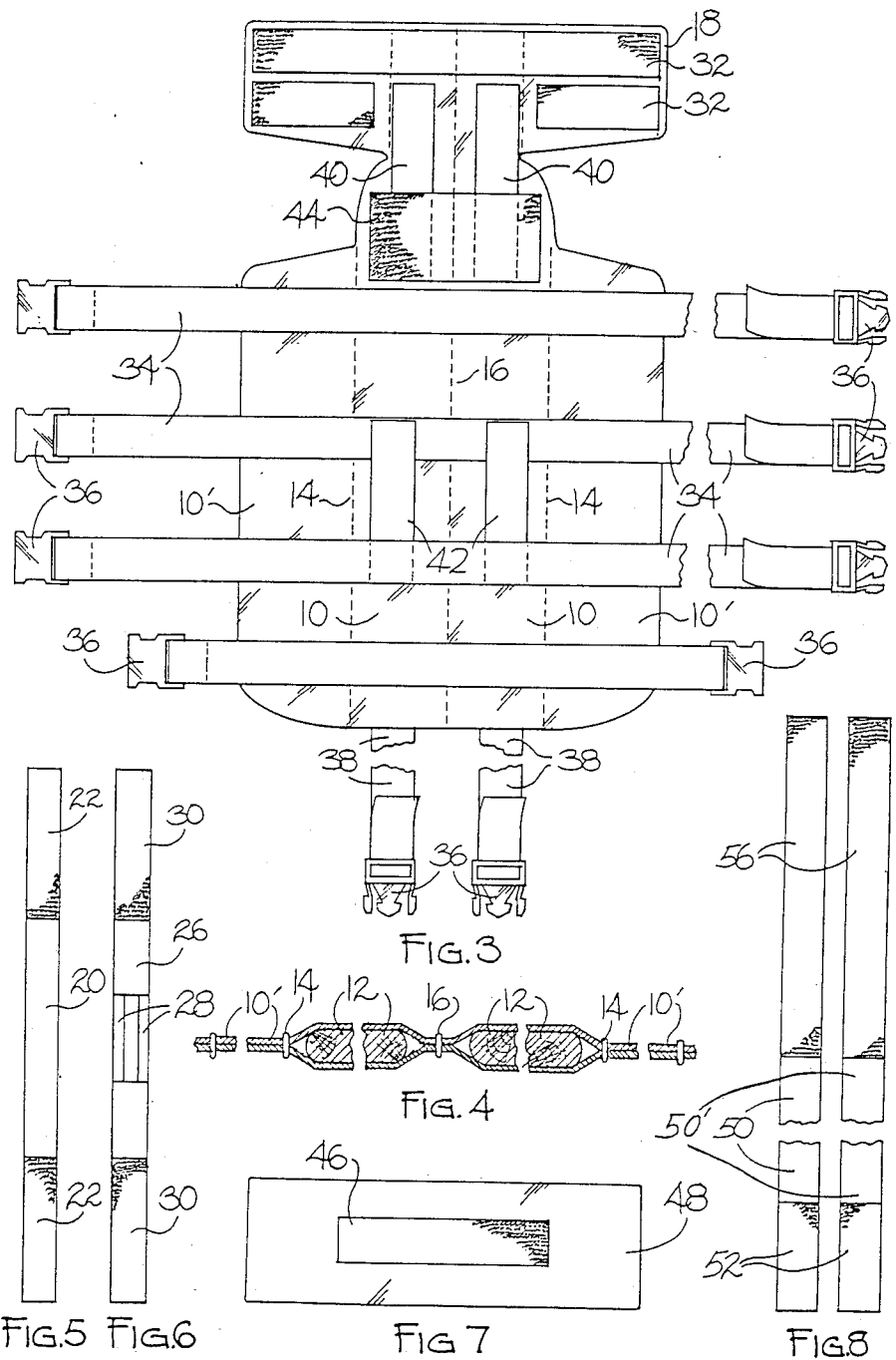

EXTRICATION AND SPINAL RESTRAINT DEVICE

BACKGROUND OF THE INVENTION

This invention relates to backboards used in emergency extrications where possible back, neck and spine injuries may exist, and more particularly to a spinal restraining apparatus which is specifically arranged with flexible sides and rigid back support configured to restrain a victim's spine securely and rigidly while avoiding the excess and painful pressures typically accompanying the use of traditional backboards on a victim's rib cage, shoulders and collarbone; areas also commonly damaged in injuries which require spinal restraint.

Emergency backboards are commonplace and are a necessary and a very frequently used tool by emergency medical aide units. Their purpose is to be applied to a victim injured in an accident whereby to immobilize the spine, neck and head when such injuries appear to be indicated. Upon immobilizing a victim, rescuers may then extricate him from the sight of the injury, transport him to a stretcher, and take him to a medical provider for treatment without concern that such movement may intensify those serious injuries.

Illustrative of typical backboards, spinal restraints and extrication devices known in the art are U.S. Pat. Nos. 4,211,218, 4,299,211, 2,788,530, 2,753,864, 2,409,195 and 1,301,276. The first three patents listed are believed to be generally pertinent to the present invention, with U.S. Pat. No. 4,211,218 being of primary interest.

U.S. Pat. No. 2,788,530 discloses a head-to-foot stretcher-like backboard, flat and rigid in construction, to which a patient is directly strapped. Head, body and foot covers, 24, 13 and 14, and 21 respectfully, are provided to drape over and cover a victim during transport in inclement conditions. U.S. Pat. No. 4,299,211 discloses an extrication splint having a rigid but deformable brace portion 2 which is arranged to be physically formed into shapes matching the particular position a victim is found in, whereupon the splint is applied to and strapped on the victim, so that his position is substantially unaltered during extrication and transport. The straps utilized to secure the victim to the splint are anchored to the brace members themselves.

In U.S. Pat. No. 4,211,218, a spinal restraint device is disclosed in which a longitudinally inflexible, laterally flexible backboard is formed of a plurality of longitudinally extending, laterally spaced apart rows of individual stiffener members arranged to wrap substantially about a victim's entire torso and be secured thereabout by cinching straps. In this regard, the longitudinally rigid stiffening members, such as board strips tightly encircle the injured torso and create inward, inflexible pressure which tends to collapse the torso inwardly and is particularly uncomfortable and medically undesirable in view of secondary injuries to bruised and broken ribs, collar bones and shoulders, etc., especially when transportation and extrication involves lifting and manipulating the victim.

SUMMARY OF THE INVENTION

In its basic concept, the extrication and spinal restraint device of this invention utilizes a flexible jacket of material configured to be wrapped partially around a victim's torso and be secured thereabout for supporting his head, neck and back, the jacket mounting a pair of longitudinally extending inflexible backbrace boards positioned to extend longitudinally along the center line of the victim's back, neck and head to provide rigid support therefor only at points spaced inwardly from the victim's sides.

It is by virtue of the foregoing basic concept that the principal objective of this invention is achieved; namely, the provision of an extrication and spinal restraint device of the class described which rigidly supports a victim's head, neck and back with braceboards while securing the victim thereto with a jacket of flexible material arranged to support the torso sides nonrigidly, thereby reducing discomfort and irritation of secondary injuries.

Another object of this invention is the provision of a spinal restraint device of the class described which also includes a removable shoulder support board arranged to retract the shoulders firmly rearward by applying traction with the use of shoulder encircling straps for more comfortable and safe transport of a victim having shoulder and collarbone injuries.

Another object of this invention is the provision of a spinal restraint device of the class described which is arranged for use with flexible extrication and transport stretchers.

Still another object of this invention is the provision of a spinal restraint device of the class described which supports the victim's back securely while allowing the victim to be moved into virtually any position that his rescuers may have to manipulate him into in the course of his rescue, without rigid support members imposing any inflexible support except along the victim's back and head so that the restraining device will not bind, jab or inflict undue pressure on the victim.

Yet another object of this invention is the provision of a spinal restraint device of the class described which is of simplified construction for economical manufacturer and reliability in use.

The foregoing and other objects and advantages of this invention will appear from the following detailed description, taken in connection with the accompanying drawings of a preferred embodiment.

BRIEF DESCRIPTION OF THE DRAWINGS

FIG. 3 is a foreshortened plan view of the outerside of the extrication and spinal restraint device seen in FIG. 2, but in open condition with the shoulder board and associated support straps not attached.

FIG. 4 is a foreshortened sectional view in reduced scale of the midportion of the spinal restraint device of this invention taken along the line 4—4 in FIG. 3.

FIG. 5 is a plan view of a head restraining forehead strap configured for use with the spinal restraint device of this invention.

FIG. 6 is a plan view of a head restraining chin strap configured for use with the spinal restraint device of this invention.

FIG. 7 is a plan view of one side of a shoulder board arranged for use with the spinal restraint device of this invention, the opposite side being identical.

FIG. 8 is a foreshortened plan view of shoulder restraining straps configured for use with the shoulder board and spinal restraint device of this invention.

DESCRIPTION OF THE PREFERRED EMBODIMENT

Figures 1, 2:
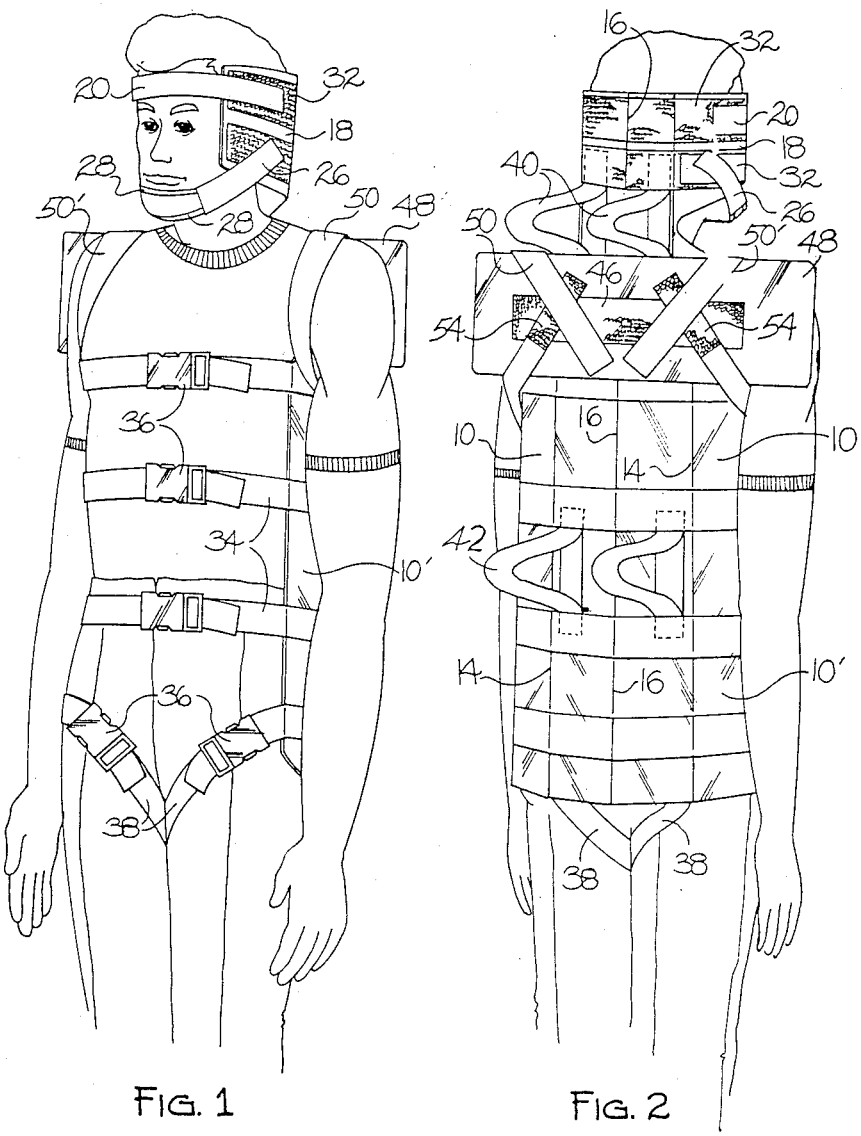
FIG. 1 is a fragmentary perspective front view of an extrication and spinal restraint device embodying the features of this invention on a victim.
FIG. 2 is a fragmentary perspective view of the extrication and spinal restraint device of FIG. 1 as would be viewed from the rear in FIG. 1.

The extrication and spinal restraint device of this invention is ideally suited for use in transporting an injured victim with the flexible stretcher disclosed is U.S. Pat. No. 4,283,068, although its use is not limited strictly to any particular stretcher type and may also be used independently of any stretcher or the like, as will become apparent from the following description.

The spinal restraint device embodied herein generally comprises a jacket of flexible material arranged to overlie the back and sides of a torso and is configured also to extend upwardly behind the neck and head, the jacket including straps which engage the opposite lateral flexible sides of the material for the purpose of securing the jacket onto a victim as viewed in FIG. 1. In order to make the jacket longitudinally inflexible so that an injured victim may be safely moved, the jacket mounts a pair of longitudinally elongated narrow backbrace boards which are configured to extend along opposite sides of the longitudinal center line of the jacket the full length thereof so as to provide rigid support only along and behind the entire length of the spine, neck and head.

More specifically, the jacket illustrated best in FIG. 3 comprises a body of reinforced cloth, plastic or other strong but flexible material 10, and contains a pair of elongated back support boards 12 in pockets formed by side and central stitchings 14 and 16, respectfully, through the material, as also seen in FIG. 8. In this regard, the pockets may be formed by stitching an additional layer of material onto the jacket in appropriate position, or the entire jacket may be formed of two identical sheets of material with stitching provided about their edges to attach them together and also stitching to form the desired pockets for maintaing the backboards 12 in proper position.

The back support members 12 thus render the central portion of the flexible jacket body 10 rigid. The portion of the jacket disposed on opposite lateral sides of the rigid central portion defined by the side stitchings 14 is devoid of stiffening members and forms lateral torso side flaps 10' which are longitudinally and laterally freely flexible for purposes which will become evident later.

The backboards 12 are of sufficient length to support the entire length of the spine and the head, as shown in FIGS. 1 and 2. As is apparent in FIGS. 2 and 3, the backboards themselves are each positioned to extend along the center line of the jacket, and are each configured preferably to be about 4 inches wide. Adjacent the base of the neck however, each of the backboards is reduced in width to about 2 inches wide for supporting the neck and the head inwardly of their sides.

The material 10 is widened in the head area in order to provide a pair of flexible head side support flaps 18 which fold forwardly about a patients head as he is rested against the rigid back support boards 12. Hence, the flexible head supports 18 are able to be wrapped rather snugly against the side of the victim's head to prevent it from turning or otherwise being moved.

Means is provided to secure a victim's head immovably against the narrowed, rigid backboards and to secure the flexible head supports 18 snugly against the victim's head. In the embodiment illustrated, this restraining means comprises a pair of straps arranged to overlie the victim's forehead and chin and be secured to the head support sections 18. A forehead strap 20 shown best in FIGS. 1 and 5, comprises a length of material arranged to overlie a victim's forehead and a portion of each side support 18. The material is preferably of a type which will not of itself irritate the skin. As shown in FIG. 5, each opposite end of the strap mounts, as by sewing, one component, preferably the loop component 22, of a Velcro type fastener. The corresponding component, the hook component 24 of the Velcro fastener, is attached to the head portion 18 of the flexible jacket, as shown in FIGS. 1, 2 and 3. Thus, the forehead strap 20 can be placed over the forehead of a victim and snugly attached to the side head support flaps 18 of the jacket to secure the victim's head immovably thereto and to draw the flaps 18 tightly against the sides of his head.

A chin support strap 26 is also preferably provided to further secure the patient's head to the head portion of the jacket. The chin strap shown best in FIGS. 1 and 6 preferably comprises two lengths of material connected together by a pair of spaced apart chin supporting strips 28, as in FIG. 6. The material 26 and 28 is also preferably of a type which will not of itself irritate the victim's skin. One component of a Velcro fastener, preferably the loop component 30, is attached to one side surface of each portion 26 adjacent its outward end for registery with a corresponding hook component 32 secured to the head support flap 18 shown in FIGS. 1 and 3. As seen best in FIG. 1, the chin support strips 28 straddle the projecting portion of the victim's chin to firmly secure the head against movement relative to the head support 18. This particular configuration of a chin support strap is particularly suitable for use with a bearded chin, since it allows the beard to project through the space between the strips 38 and thus prevents inadvertent slipping of the strap during movement of the patient away from the scene of an accident.

Means is also provided to secure the flexible torso flap portion 10' of the board supporting jacket onto an injured person so that backboards 12 are retained in proper position extending centrally along the victim's spine, the central stitching 16 being disposed directly over the victim's spine. In this embodiment, three chest straps 34 are provided at longitudinally spaced intervals along the jacket 10' and securely stitched to the flexible material. By virtue of their being stitched to the non-rigid lateral side flaps 10' of the jacket, the chest straps 34 overlie the victim's chest and waist and, together with the jacket, encircle the torso so that when the straps are fastened together, as by buckles 36, the flexible side portions 10' support the patient's sides equally and snuggly, but non-rigidly.

Leg straps 38 are attached to the lower end of the jacket for engaging the legs at the crotch, as viewed in FIGS. 1 and 2, in order to further secure the restraining device onto the patient and to prevent longitudinal movement of the patient relative to the device during transport.

Thus, from the foregoing, it is apparent that, unlike spinal restraints of the prior art, a victim is secured to the extrication and spinal restraint device of this invention by various head and torso straps 20, 26, 34 and 38 which are themselves secured only to the flexible portions 10' of the restraint jacket rather than to a rigid portions 10 as is typically done.

In order to facilitate the victim's extrication and transport, the spinal restraint device of the present invention includes means engaging the rigid portion 10 of the jacket whereby rescuers may safely lift and carry a victim secured immovably by the device. As seen best in FIGS. 2 and 3, a pair of upper lifting straps 40 are secured to the jacket material over the rigid backboard portion adjacent the upper shoulders and neck, and a pair of lower lifting straps 42 are secured on the jacket material over the rigid back supporting boards adjacent the victim's lower back. The lifting straps 40, 42 are thus readily available to two rescuers, one on each side of the victim, for carrying him between them.

The extrication and spinal restraint device of this invention also includes means for immobilzing a victim's shoulders in proper condition when a broken collarbone or shoulder is present. As seen in FIG. 3, one component 44 of a Velcro fastener, preferably the loop component, is attached to the outside of the jacket over the rigid portion 10 thereof behind the shoulder area. This Velcro component is arranged to receive the corresponding component 46, preferably the hook component of a fastener disposed on one side of an elongated shoulder board 48 as viewed in FIG. 4, to secure the board in the laterally extending position of FIGS. 1 and 2. The opposite side of the shoulder board also mounts a hook component 46 similar to that which is disposed on the one side for purposes which will be explained presently.

Shoulder straps 50, 50' provide means by which a victim's shoulders are releasably secured to the rigid shoulder board 48. As illustrated in FIG. 8, a pair of elongated straps, which preferably do not irritate the skin, are configured of sufficient length so as to extend from the shoulder board 48 around a victim's shoulder, thence under the armpit and back to the shoulder board as in FIGS. 1 and 2, and to accommodate virtually any size individual being strapped therewith. As is apparent from FIGS. 2 and 8, one end of each strap, the bottom in FIG. 8 mounts a relatively short length of loop component 52 of a Velcro type fastener arranged to engage the corresponding hook component 46 on the shoulder board, as seen in FIG. 2. On the side surface opposite the loop component 52 on the end of the shoulder strap 50,50' is affixed a length of Velcro hook component 54. Thus, when the end of the shoulder strap having the loop component 52 is attached to the shoulder board 48, the opposite side surface of the strap exposes Velcro hooks 54 similar to the component 46 afixed to the shoulder board 48.

The end of the shoulder strap opposite the aforementioned lower end mounts, on the same side surface having the loop compnent 52, a length of Velcro loop 56. As is apparent from the drawing, this loop component preferably extends a substantial length along the shoulder strap in order to provide a wide range of adjustability of the strap. As is seen in FIG. 2, the shoulder strap, after being attached to the shoulder board, is drawn under the victim's arm pit, up and around his shoulder, and drawn back over the shoulder board so that the longer length of loop component 56 may engage the Velcro hook component 46 on the shoulder board and the hook component 54 on the end of the shoulder strap attached thereto.

In this manner, the victim's shoulders are drawn rearward toward the shoulder board, applying traction to pull the collarbone from an overlapped position into an end-to-end position and immobilizing them in that medically sound condition, further reducing discomfort.

Use of the shoulder board in the manner described above also affords another advantage particularly valuable in the use of flexible stretchers of the type disclosed in the aforementioned U.S. Pat. No. 4,283,068. With the shoulder board 48 thus secured to the spinal restraint device, the shoulders are immobilized in an outstretched, flat position. This prevents the inward collapse of the flexible stretcher sides during lifting and transporting and prevents movement of shoulders when using flexible stretchers.

The shoulder board, when not required in its aforementioned capacities, may be alternatively used as an arm splint, short leg splint and other types of splints by simply applying it against a facture and wrapping the shoulder straps 50,50' thereabout to secure the board in place.

From the foregoing it is apparent that the present invention provides a unique spinal restraint device which rigidly supports a victim's spine, neck and head only inwardly of his sides, and non-rigidly supports the victim's sides while utilizing the non-rigid sides 10' to provide means by which the restraining device is strapped to the victim's body. No other spinal restraint device system is known which is arranged to support an injured victim in a similar fashion.

The operation of the extrication and spinal restraint device described is as follows: After access to an injured victim has been gained, and possible injuries have been determined, the spinal restraint device is unfolded into the open position in FIG. 3 and positioned behind the victim's back so that the central stitching 16 between the back brace boards 12 extends along the victim's spine. In the event of possible neck injury, a conventional cervical collar (not shown) would be applied to the victim. The victim's head is then immobilized by folding one side head support 18 inwardly against the head, applying one end of the forehead strap 20 to the Velcro component 24 attached thereto, bringing the opposite side head support flap 18 against the other side of the victim's head and snuggly attaching the opposite end of the forehead strap to the Velcro componnent 24 on the latter side head support flap. The chin strap 26 then is applied, as described, making sure that the chin strips 30 are secured so as to straddle the projecting portion of the victim's chin.

In the event the victim's head is in a position which suggests that movement of his head is not desired, padding would be applied between the victim's head and the head portion of the spinal restraint prior to securing his head thereto with the forehead and chin straps, rather than attempting to manipulate his neck in the field. The torso portion is then ready to be secured.

With the stitching 16 of the jacket 10 aligned centrally along the victim's spine, the flexible side support flaps 10' are drawn about the victim's sides, the corresponding chest straps 34 are buckled together and cinched snugly, and the leg straps 38 are applied and cinched. If necessary the shoulder board 48 is then applied.

The shoulder board is brought behind the victim's shoulders and positioned vertically to the desired height location behind the victim's shoulders. The Velcro component 44 (FIG. 3) is configured of sufficient width to allow a range of vertical adjustment of the board to accommodate persons of various heights. When properly positioned, the board is pressed against the jacket whereupon the corresponding Velcro fasteners 44 on the jacket and 46 on the shoulder board, engage to secure the board in the desired position. The shoulder straps 50,50' are applied as discussed above by engaging the corresponding Velcro components 46 on the shoulder board and 52 on the one end of the shoulder strap. Each shoulder strap is then drawn under the victim's arm pit and upwardly around his shoulder, drawing the shoulder flat against the shoulder board, whereupon the Velcro component 56 on the free end of the shoulder strap engages the exposed, corresponding Velcro components 46,54 on the shoulder board and strap end attached thereto. The victim, thus secured immovably to the spinal restraint device, is ready for extrication and transport to a medical provider. This also provides greater security against movement of the spine.

The rescuers may then manipulate the victim by grasping the lifting straps 40,42 provided on the rigid portion 10 of the device. The victim may be lifted vertically from a sitting position or vertically from a reclining position or may be lifted and carried in a downwardly facing position, if required. In any case, there is no imposition of rigid boards pressing against tender sides, chest, rib cage and potentially injured organs.

When the restraint device has been removed from a victim at a hospital, the straps 20, 26, 34, 38, 50 and 50' may be folded and laid over the flexible side flaps 10' and the flaps folded along stitch line 14 against boards 12. The rigid board sections then may be hinged along central stitch line 16 so that they fold and all of the straps are contained within the folded flaps 10'. The resulting package, unlike other backboards of the prior art, is very compact in size, about 5 inches wide, about 3 inches deep, and approximately 33 inches long, making the device extremely convenient to store. A carrying case, (not shown) similar in appearance to a soft rifle case, may be provided to carry the device and the separate shoulder board when not in use.

From the foregoing it is apparent that various changes may be made in the size, shape, type, number and arrangement of parts described hereinbefore without departing from the spirit of this invention and the scope of the appended claims. For example, although Velcro fasteners and buckles have been described throughout and their use is considered to be preferred, it is to be understood that other fastening means may be employed as an alternative. Also, it is to be understood that the particular configuration of the jackect which supports the pair of back brace boards inwardly of the victim's sides is not intended to be limited strictly to that shown. Other jacket configurations and specifications could be employed to accomplish the specific goals discussed hereinbefore.

Having thus now described my invention and the manner in which it may be used, I claim:

1. A spinal restraint device, comprising:
   (a) two and only two elongated, parallel, rigid back brace members joined together along their adjacent longitudinal edges for longitudinal folding against each other,
   (b) said back brace members having a length sufficient to extend from the base of the spine of a human torso to the back of the head and a combined width less than the width of a human torso or head,
   (c) a pair of longitudinally and laterally flexible torso flap members, one of said torso flap members being secured to the non-adjacent longitudinal edge of each back brace member and extending laterally of each of the back brace members, said torso flap members being configured to extend flexibly along the sides of a human torso from adjacent the arm pits downward to a point adjacent the hips,
   (d) a pair of longitudinally and laterally flexible head flap members, one of said head flap members being secured to and extending laterally of the non-adjacent edge of each of the back brace members, said head flap members being configured to extend flexibly along substantially the full length of the sides of a human head, and
   (e) a plurality of longitudinally spaced flexible torso and head flap securing means secured to said torso and head flap members, respectively, and arranged to extend therefrom across the front of a human torso and head, respectively, for securing the flap members along the sides of the torso and head, respectively.

2. The spinal restraint device of claim 1 including two pairs of lifting handle members secured to the back brace members one pair adjacent the head ends thereof and the other pair adjacent the bottom ends thereof.

3. The spinal restraint device of claim 1 including a pair of leg securing strap members secured to the bottom ends of the back brace members and arranged to encircle the legs extending from a human torso.

4. The spinal restraint device of claim 1 wherein the flexible head strap securing means includes an elongated flexible strap having an intermediate centrally open portion defining a pair of flexible strips arranged to span upper and lower spaced portions of the chin.

5. The spinal restraint device of claim 1 including a rigid shoulder support member arranged for removable attachment and to extend laterally to opposite sides of the back brace members in the area of the shoulders of a human torso, and a pair of flexible shoulder strap members arranged for encircling the shoulders and releasable attachment to the shoulder support member for supporting and restraining the shoulders against the shoulder support member.

6. The spinal restraint device of claim 1 including a longitudinally and laterally flexible body having a pair of pockets extending longitudinally along opposite sides of the longitudinal center line of the body and configured to removably receive the pair of rigid back brace members therein, the portions of the flexible body extending laterally to opposite sides of the pockets defining said torso and head flap members, the flexible body between the pockets forming a folding hinge between the adjacent longitudinal edges of the back brace members whereby the latter may be folded against each other.

7. The spinal restraint device of claim 6 including two pairs of lifting handle members secured to the body in the area of the back brace member pockets one pair adjacent the head end thereof and the other pair adjacent the bottom end thereof.

8. The spinal restraint device of claim 6 including a pair of leg securing strap members secured to the body in the area of the bottom ends of the back brace member pockets and arranged to encircle the legs extending from a human torso.

9. The spinal restraint device of claim 6 including a rigid shoulder support member arranged for removable attachment to the body and to extend laterally to opposite sides of the back brace member pockets in the area of the shoulders of a human torso, and a pair of flexible shoulder strap members arranged for encircling the shoulders and releasable attachment to the shoulder support member for supporting the shoulders against the shoulder support member.

* * * * *